(12) United States Patent  
Muto et al.

(10) Patent No.: US 7,411,076 B2
(45) Date of Patent: Aug. 12, 2008

(54) COUMARIN DERIVATIVE

(75) Inventors: Susumu Muto, Tokyo (JP); Masayuki Komukai, Chiba (JP); Akiko Itai, Tokyo (JP)

(73) Assignee: Institute of Medicinal Molecular Design, Inc., Tokyo (JP)

( * ) Notice: Subject to any disclaimer, the term of this patent is extended or adjusted under 35 U.S.C. 154(b) by 387 days.

(21) Appl. No.: 10/488,254

(22) PCT Filed: Sep. 12, 2002

(86) PCT No.: PCT/JP02/09339

§ 371 (c)(1),
(2), (4) Date: Sep. 23, 2004

(87) PCT Pub. No.: WO03/024950

PCT Pub. Date: Mar. 27, 2003

(65) Prior Publication Data

US 2005/0054717 A1   Mar. 10, 2005

(51) Int. Cl.
C07D 311/16 (2006.01)
C07D 409/12 (2006.01)
C07D 405/12 (2006.01)
C07C 407/12 (2006.01)

(52) U.S. Cl. .................. 549/285; 560/21; 560/22; 514/299

(58) Field of Classification Search .......... None
See application file for complete search history.

(56) References Cited

FOREIGN PATENT DOCUMENTS

| EP | 1402890 | 3/2004 |
| JP | 10-182647 | 7/1993 |
| WO | 93/16064 | 8/1993 |

OTHER PUBLICATIONS

The Merck Manual of Diagnosis and therapy, seventeenth edition, 1999, Published by Merk Research Laboratories pp. 397-398, 948-949, 1916 and 1979-1981.*
J. Biol. Chem. 275, pp. 5600-5605, 2000.
J. Biol. Chem. 276, 17693-17698, 2001.
Jpn. J. Cancer Res. 80, pp. 83-88, 1989.
Invest. New Drugs 18, pp. 95-107, 2000.
J. Biol. Chem. 275, pp. 10342-10348, 2000.
Cancer Res. 61, pp. 1065-1072, 2001.
Cancer Res. 60, pp. 2108-2112, 2000.
Cancer Res. 59, pp. 4375-4382, 1999.
Biochem. Biophys. Res. Commun. 219, pp. 778-783, 1996.
Acta. Pharmacol. Sin. 21, pp. 35-40, 2000.
J. Heterocycl. Chem. 26, pp. 1273-1275, 1989.
Merck Manual of Diagnosis and Therapy, Seventeenth Edition, pp. 986-995, 1999.
English Language Abstract of JP 10-182647.
Farmaco, Ed. Sci. 36, pp. 565-584, 1981.

* cited by examiner

*Primary Examiner*—Yvonne Eyler
*Assistant Examiner*—Yevegeny Valenrod
(74) *Attorney, Agent, or Firm*—Greenblum & Bernstein, P.L.C.

(57) ABSTRACT

A medicament for enhancing an effect of a cancer therapy based on a mode of action of DNA injury, which comprises as an active ingredient a compound represented by the following general formula (I):

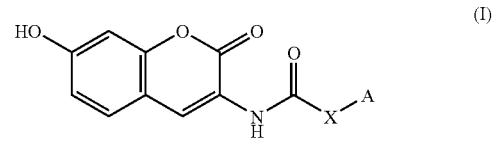

wherein X represents a single bond or a $C_1$ to $C_6$ alkylene group which may be substituted; A represents a $C_1$ to $C_6$ alkyl group which may be substituted, a $C_6$ to $C_{10}$ aryl group which may be substituted, or a 4 to 10-membered monocyclic or bicyclic and unsaturated, partly saturated, or completely saturated heterocyclic group which may be substituted, wherein said heterocyclic group comprises as ring-constituting atoms 1 to 4 hetero atoms selected from the group consisting of nitrogen atom, oxygen atom, and sulfur atom.

2 Claims, No Drawings

COUMARIN DERIVATIVE

FIELD OF INVENTION

The present invention relates to medicaments for enhancing the effect of cancer therapy on the basis of mechanism of injuring DNA, and novel compounds useful as active ingredients of said medicament.

BACKGROUND ART

Anticancer agents are administered in treatments of cancer patients at present. However, their life-prolongation rates are undesirably low, and moreover, cancer patients administered with an anticancer agent are forced to tolerate severe side effects such as fever, nausea, epilation, chill, fatigue, immune malfunction, gastrointestinal disorder, liver disorder, and kidney disorder, which becomes a cause of significant deterioration of the QOL (Quality of Life) of the cancer patients. Furthermore, reduction of sensitivity of cancer cells to anticancer agents, caused by the use of the anticancer agents, may lead to prolonged administration period of administration of the anticancer agents and increase of doses, and as a result, deaths resulting from side effects of the anticancer agents are often observed. Therefore, the administration of anticancer agents may spoil advantages of patients, as well as significantly diminish social and economic benefits. This is caused by the fact that anticancer agents, which are expectedly used to exhibit selective cytotoxicity to cancer cells that disorderly divide and proliferate, actually act cytotoxically on normal cells, particularly on cells in the intestine and marrow.

In recent years, reports have been made on caffeine which is a low molecule organic compound and UCN-01 (7-hydroxy staurosporine) having actions to enhance radiation susceptibility of cancer cells which are radiation resistant (J. Biol. Chem., 275, 5600-5605, 2000; J. Biol. Chem., 276, 17693-17698, 2001). Cancer therapy by radiation is also based on the mode of action of artificial injury of DNAs, and is considered to be basically equivalent to anticancer agents such as bleomycin based on the mode of action of DNA injury. Accordingly, it is believed that a drug that enhances selective toxicity to cancer cells can be developed even for anticancer agents based on the mode of action of DNA injury which are available at present.

In fact, it is reported that caffeine increases the actions of anticancer agents such as adriamycin, cisplatin, cyclophosphamide, and mitomycin C based on the mode of action of DNA injury (Jpn. J. Cancer. Res., 80, 83-88, 1989). However, potency remains insufficient, and separation from toxicity is unsatisfactory. UCN-01 is also reported to enhance actions of several kinds of anticancer agents based on the mode of action of DNA injury (Invest. New Drugs, 18, 95-107, 2000).

As for the mode of action of the potentiation of anticancer agents, the action is presumed to be based on a destruction of a certain part of the cell cycle (for example, G1 period and G2 period: Cancer Res., 60, 2108-2112, 2000; Cancer Res., 59, 4375-4382(1999), since caffeine and UCN-01 inhibit protein kinases involved in a control of a cell cycle (J. Biol. Chem., 275, 10342-10348, 2000; Cancer Res., 61, 1065-1072, 2001). However, no conclusive evidence has been obtained. In addition, since caffeine and UNC-01 as a staurosporin derivative have inhibitory actions against multiple kinds of protein kinases (Biochem. Biophys. Res. Commun., 219, 778-783, 1996; Acta Pharmacol. Sin., 21, 35-40, 2000), a possibility of involvement of a mechanism other than the destruction of the cell cycle can not be denied. Accordingly, a clear mode of action remains unidentified. Furthermore, there is a high possibility that these agents have inhibitory actions also against protein kinases participating in intracellular signal transduction, which is considered to be a possible cause of inducing serious side effects.

As explained above, no effective means is available at present to solve various problems caused by the cancer therapies based on the mode of action of DNA injury. Developments of new drugs or therapies, that potentiate the effects of available anticancer agents and radiation therapy based on the mode of action of DNA injury and that enhance selectivity to cancer cells to decrease side effects, will contribute to increase the QOL and advantages of cancer patients as well as social and economic benefits.

DISCLOSURE OF THE INVENTION

An object of the present invention is to provide medicaments for enhancing the effect of cancer therapy based on the mode of action of DNA injury. More specifically, an object of the present invention is to provide medicaments which, per se, have weak anticancer activity (cytotoxicity), but in combination of an anticancer agent based on the mode of action of DNA injury or a therapy such as radiation which gives artificial injuries to DNA, can selectively damage or kill cancer cells at a lower dose of anticancer agent or a lower radiation dose so as to significantly reduce affects on normal cells. Furthermore, another object of the present invention is to provide medicaments to reduce side effects resulting from cancer therapy by potentiation of the effects of the above cancer therapy and by reduction of a dose of the anticancer agent and/or radiation dose. Still further object of the present invention is to provide novel compounds which are useful as active ingredients of the above medicaments.

The inventors of the present invention focused on protein kinase inhibitors to solve the aforementioned objects, and carried out search for compounds having desired pharmacological activities by using computerized molecular design technology as a means to discover candidate compounds. The inventors carried out an automatic search program of a ligand from a three-dimensional compound database based on the three-dimensional structure of the protein by using the ATP binding regions of several kinds of protein kinases whose structures are registered in PDB (Protein Data Bank), and by virtual screenings, they selected compounds having potentials as protein kinase inhibitors from compounds registered in databases of commercial compounds. The inventors classified the resulting compounds on the basis of their skeletons, and by using several typical compounds, they carried out tests of combined effects with bleomycin on cancer cells and normal cells and tests of cytotoxicity to cancer cells and normal cells when the compounds are used alone. The inventors selected compounds having strong and desired pharmacological activities, and further prepared their derivatives to achieve the present invention.

The present invention thus provides a medicament for enhancing an effect of a cancer therapy based on a mode of action of DNA injury which comprises as an active ingredient a compound represented by the general formula (I) and a physiologically acceptable salt thereof, and a hydrate thereof and a solvate thereof:

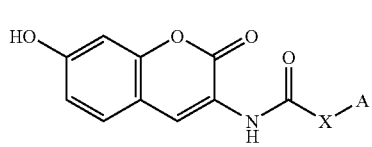 (I)

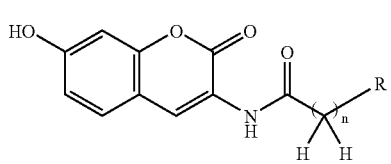 (II)

wherein X represents a single bond or a $C_1$ to $C_6$ alkylene group which may be substituted; A represents a $C_1$ to $C_6$ alkyl group which may be substituted, a $C_6$ to $C_{10}$ aryl group which may be substituted, or a 4 to 10-membered monocyclic or bicyclic and unsaturated, partly saturated, or completely saturated heterocyclic group which may be substituted, wherein said heterocyclic group comprises as ring-constituting atoms 1 to 4 hetero atoms selected from the group consisting of nitrogen atom, oxygen atom, and sulfur atom.

According to preferred embodiments of the present invention, provided are the aforementioned medicament wherein the cancer therapy based on the mode of action of DNA injury is carried out by administration of an anticancer agent and/or radiation; the aforementioned medicament wherein the anticancer agent is selected from a group consisting of bleomycin, adriamycin, cisplatin, cyclophosphamide, mitomycin C, and their derivatives; and the aforementioned medicament which is a specific inhibitor against a protein kinase and/or its analogous enzyme.

From another aspect, the present invention provides a medicament for reducing a side effect resulting from a cancer therapy based on the mode of action of DNA injury which comprises as an active ingredient a compound represented by the aforementioned general formula (I) or a physiologically acceptable salt thereof.

From further another aspect, the present invention provides use of the compound represented by the aforementioned general formula (I) or the physiologically acceptable salt thereof for manufacture of the aforementioned medicament; a method of enhancing an effect of cancer therapy based on the mode of action of DNA injury in a mammal including a human, which comprises the step of applying a cancer therapy based on the mode of action of DNA injury to a cancer patient, and the step of administering the compound represented by the aforementioned general formula (I) or the physiologically acceptable salt thereof at a dose sufficient to potentiate the effect of the aforementioned cancer therapy; a method of reducing a side effect resulting from a cancer therapy based on the mode of action of DNA injury in a mammal including a human, which comprises the step of applying a cancer therapy based on the mode of action of DNA injury to a cancer patient, and the step of administering the compound represented by the aforementioned general formula (I) or the physiologically acceptable salt thereof at a dose sufficient to reduce the side effect of the aforementioned cancer therapy.

Furthermore, the present invention provides, a compound represented by the general formula (II) or a salt thereof:

wherein n represents an integer of from 0 to 2; R represents a $C_1$ to $C_6$ alkyl group which may be substituted, a $C_6$ to $C_{10}$ aryl group which may be substituted, or a 4 to 10-membered monocyclic or bicyclic and unsaturated, partly saturated, or completely saturated heterocyclic group which may be substituted, wherein said heterocyclic group comprises as ring-constituting atoms 1 to 4 hetero atoms selected from the group consisting of nitrogen atom, oxygen atom, and sulfur atom; provided that the compound wherein n is 0; and R is unsubstituted phenyl group, 4-methylphenyl group, 3-(trifluoromethyl)phenyl group, 4-methoxyphenyl group, 2,4-dichlorophenyl group, or methyl group is excluded.

Furthermore, the present invention provides a medicament comprising as an active ingredient a compound represented by the aforementioned general formula (II) or a physiologically acceptable salt thereof. This medicament can be used as a medicament to potentiate the effect of cancer therapy based on the mode of action of DNA injury. According to preferred embodiments of the present invention, provided are the aforementioned medicament wherein the cancer therapy based on the mode of action of DNA injury is carried out by the administration of an anticancer agent and/or radiation; the aforementioned medicament wherein the anticancer agent is selected from the group consisting of bleomycin, adriamycin, cisplatin, cyclophosphamide, mitomycin C, and their derivatives; and the aforementioned medicament which is a specific inhibitor of a protein kinase and/or analogous enzyme thereof.

From another aspect, the present invention provides a medicament which comprises the compound represented by the aforementioned general formula (II) or the physiologically acceptable salt thereof as an active ingredient, and which reduces a side effect resulting from a cancer therapy based on the mode of action of DNA injury.

From further another aspect, the present invention provides use of the compound represented by the aforementioned general formula (II) or the physiologically acceptable salt thereof for manufacture of the aforementioned medicament; a method of enhancing the effect of a cancer therapy based on the mode of action of DNA injury in a mammal including a human, which comprises the step of applying a cancer therapy based on the mode of action of DNA injury to a cancer patient and the step of administering the compound represented by the aforementioned general formula (II) or the physiologically acceptable salt thereof at a dose sufficient to potentiate the effect of the aforementioned cancer therapy; a method of reducing a side effect resulting from a cancer therapy based on the mode of action of DNA injury in a mammal including a human, which comprises the step of applying a cancer therapy based on the mode of action of DNA injury to a cancer patient and the step of administering the compound represented by the aforementioned general formula (II) or the physiologically acceptable salt thereof at a dose sufficient to potentiate the effect of the aforementioned cancer therapy.

BEST MODE FOR CARRYING OUT THE INVENTION

The terms used in the present specification have the following meanings.

The alkyl group may be straight chain, branched chain, cyclic, and combination of these unless otherwise specifically mentioned. More specifically, examples include methyl group, ethyl group, n-propyl group, isopropyl group, cyclopropyl group, n-butyl group, isobutyl group, sec-butyl group, tert-butyl group, cyclobutyl group, cyclopropylmethyl group, n-pentyl group, isopentyl group, neopentyl group, tert-pentyl group, cyclopentyl group, n-hexyl group, cyclohexyl group, 3,3-dimethylbutyl group, 2-ethylbutyl group, 2-methylpentyl group, 3-methylpentyl group, or 4-methylpentyl group. An alkyl moiety of other substituents containing the alkyl moiety have the same meaning.

When X is a single bond, said option means that A and carbonyl carbon are directly bonded. Furthermore, when n is 0, said option means that R and carbonyl carbon are directly bonded. The $C_1$ to $C_6$ alkylene group may have a branched chain or a cyclic structure. Preferably, a straight chain alkylene group may be used. The $C_6$ to $C_{10}$ aryl group may either be monocyclic or fused cyclic. Examples include phenyl group, 1-naphthyl group, and 2-naphthyl group.

Examples of the 4 to 10-membered monocyclic or bicyclic and unsaturated, partly saturated, or completely saturated heterocyclic group, which comprises as ring-constituting atoms 1 to 4 hetero atoms selected from the group consisting of nitrogen atom, oxygen atom, and sulfur atom, include thienyl group, furyl group, pyrrolyl group, oxazolyl group, isoxazolyl group, thiazolyl group, imidazolyl group, pyrazolyl group, benzothiophenyl group, benzofuranyl group, isobenzothiophenyl group, isobenzofuranyl group, indolyl group, isoindolyl group, indolizinyl group, 1H-indazolyl group, purinyl group, benzothiazolyl group, benzoxazolyl group, benzimidazolyl group, 1,2,3-thiadiazolyl group, 1,2,4-thiadiazolyl group, 1,3,4-thiadiazolyl group, 1,3,4-oxadiazolyl group, 1,2,3-triazolyl group, 1,2,4-triazolyl group, tetrazolyl group, chromenyl group, pyridyl group, pyridazinyl group, pyrimidinyl group, pyrazinyl group, quinolizinyl group, quinolyl group, isoquinolyl group, phthalazinyl group, naphthyridinyl group, quinoxalinyl group, quinazolinyl group, cinnolinyl group, pteridinyl group, 1,2,4-triazinyl group, chromanyl group, isochromanyl group, azetidinyl group, 2-oxoazetidinyl group, pyrrolidinyl group, pyrrolinyl group, imidazolidinyl group, imidazolinyl group, pyrazolidinyl group, pyrazolinyl group, piperidyl group, piperazinyl group, morpholino group, morpholinyl group, thiomorpholino group, thiomorpholinyl group, indolinyl group, isoindolinyl group, 1,2,3,4-tetrahydroquinolyl group, quinuclidinyl group, and methylenedioxyphenyl group.

In the present specification, when a certain functional group is defined as "which may be substituted", kinds, numbers, and positions of substituents existing in the functional groups are not particularly limited. Examples of these substituents include halogen atoms (any of fluorine atom, chlorine atom, bromine atom, or iodine atom may be used), hydroxy group, a $C_1$ to $C_6$ alkyl group, a $C_2$ to $C_6$ alkenyl group, a $C_2$ to $C_6$ alkynyl group, a $C_6$ to $C_{10}$ aryl group, a $C_7$ to $C_{12}$ aralkyl group, a $C_1$ to $C_8$ hydroxyalkyl group, trifluoromethoxy group, a $C_1$ to $C_6$ alkoxy group, a $C_2$ to $C_6$ alkenyloxy group, a $C_2$ to $C_6$ alkynyloxy group, a $C_8$ to $C_{10}$ aryloxy group, a $C_7$ to $C_{12}$ aralkyloxy group, a $C_1$ to $C_6$ hydroxyalkyloxy group, a $C_1$ to $C_6$ alkanoyl group, a $C_6$ to $C_{10}$ aroyl group, carboxy group, a $C_1$ to $C_6$ alkoxycarbonyl group, carbamoyl group, thiol group, a $C_1$ to $C_6$ alkylthio group, a $C_6$ to $C_{10}$ arylthio group, a $C_7$ to $C_{12}$ aralkylthio group, a $C_1$ to $C_6$ hydroxyalkylthio group, sulfonic acid group, a $C_1$ to $C_6$ alkylsulfonyl group, a $C_6$ to $C_{10}$ arylsulfonyl group, sulfamoyl group, formyl group, hydroxyimino group, a $C_1$ to $C_6$ alkoxyimino group, phenoxyimino group, cyano group, nitro group, amino group, formylamino group, a $C_1$ to $C_6$ alkanoylamino group, a $C_6$ to $C_{10}$ aroylamino group, a $C_1$ to $C_6$ alkoxycarbonylamino group, a $C_1$ to $C_6$ alkylsulfonylamino group, a $C_6$ to $C_{10}$ arylsulfonylamino group, amidino group, guanidino group, silyl group, stannyl group, and a heterocyclic group.

Specific examples of these substituents, in addition to the aforementioned alkyl group, aryl group, or heterocyclic group, include, for example, a $C_7$ to $C_{12}$ aralkyl group such as benzyl group, phenethyl group, 1-naphthylmethyl group, 2-naphthylmethyl group, 1-naphthylethyl group, or 2-naphthylethyl group; a $C_1$ to $C_6$ alkoxy group such as methoxy group, ethoxy group, or n-propoxy group; a $C_6$ to $C_{10}$ aryloxy group such as phenoxy group, 1-naphthyloxy group, or 2-naphthyloxy group; a $C_7$ to $C_{12}$ aralkyloxy group such as benzyloxy group, phenethyloxy group, (1-naphthylmethyl)oxy group, or (2-naphthylmethyl)oxy group; a $C_1$ to $C_6$ alkanoyl group such as acetyl group, propionyl group, or n-butyryl group; a $C_6$ to $C_{10}$ aroyl group such as benzoyl group, 1-naphthoyl group, or 2-naphthoyl group; a $C_1$ to $C_6$ alkoxycarbonyl group such as methoxycarbonyl group, ethoxycarbonyl group, or n-propoxycarbonyl group; a $C_1$ to $C_6$ alkylthio group such as methylthio group, ethylthio group, or n-propylthio group; a $C_6$ to $C_{10}$ arylthio group such as phenylthio group, 1-naphthylthio group, or 2-naphthylthio group; a $C_1$ to $C_6$ alkylsulfonyl group such as methanesulfonyl group, ethanesulfonyl group, or propanesulfonyl group; and a $C_6$ to $C_{10}$ arylsulfonyl group such as benzenesulfonyl group, 1-naphthalenesulfonyl group, or 2-naphthalenesulfonyl group.

These substituents may further be substituted with the aforementioned substituents. Examples include a halogenated alkyl group, a halogenated alkoxy group, a carboxy-substituted alkyl group, and an alkyl-substituted amino group. Furthermore, two or more substituents of the aforementioned substituents may form a ring together with the atoms to which they bind (carbon atom, nitrogen atom, boron atom, and the like). In these rings, one or more hetero atoms selected from the group consisting of nitrogen atom, oxygen atom, and sulfur atom may be included as ring-constituting atoms, and one or more substituents may exist on the ring. The ring may either be monocyclic or fused cyclic, or may be unsaturated, partly saturated, or completely saturated.

The compounds represented by the general formulas (I) or (II) may form salts. As the physiologically acceptable salt, when acidic groups exist, examples include metal salts such as lithium salt, sodium salt, potassium salt, magnesium salt, and calcium salt, or ammonium salts such as ammonium salt, methylammonium salt, dimethylammonium salt, trimethylammonium salt, and dicyclohexylammonium salt, and when basic groups exist, examples include mineral acid salts such as hydrochloride, hydrobromide, sulfate, nitrate, and phosphate, or organic acid salts such as methane sulfonate, benzene sulfonate, para-toluene sulfonate, acetate, propionate, tartrate, fumarate, maleate, malate, oxalate, succinate, citrate, benzoate, mandelate, cinnamate, and lactate. Salts may sometimes be formed with amino acids such as glycine. As active ingredients of the medicaments of the present invention, physiologically acceptable salts are suitable.

The compounds or salts thereof represented by the general formulas (I) or (II) may exist as hydrates or solvates. As an active ingredient of the medicament of the present invention, any of the aforementioned substances may be used. Furthermore, the compounds represented by the general formulas (I) or (II) may sometimes have one or more asymmetric carbons, and may exist as stereoisomers such as optically active isomers and diastereomers. As active ingredients of the medicaments of the present invention, a pure form of a stereoisomer, any mixture of enantiomers or diastereomers, a racemate or the like may be used. Furthermore, when the compounds represented by the formulas (I) or (II) have an olefinic double bond, its configuration may be in either E or Z. As an active ingredient of the medicament of the present invention, a geometrical isomer in either of the configurations or a mixture thereof may be used.

Examples of the preferred compounds as active ingredients of the medicaments of the present invention are shown below. However, the active ingredients of the medicaments of the present invention are not limited to the following compounds.

[Structure: 7-hydroxy-coumarin-3-yl-NH-C(=O)-(CH₂)ₙ-CHR-]

| Compound Number | R | n |
|---|---|---|
| 1 | phenyl | 0 |
| 2 | 2-chlorophenyl | 0 |
| 3 | 3-chlorophenyl | 0 |
| 4 | 3-bromophenyl | 0 |
| 5 | 4-chlorophenyl | 0 |
| 6 | 4-fluorophenyl | 0 |
| 7 | 3,4-dichlorophenyl | 0 |
| 8 | 2-methylphenyl | 0 |
| 9 | 3-methylphenyl | 0 |
| 10 | 4-methylphenyl | 0 |
| 11 | 4-tert-butylphenyl | 0 |
| 12 | 3-trifluoromethylphenyl | 0 |
| 13 | 4-trifluoromethylphenyl | 0 |
| 14 | 4-biphenyl | 0 |
| 15 | 2-methoxyphenyl | 0 |
| 16 | 3-methoxyphenyl | 0 |
| 17 | 3,4-dimethoxyphenyl | 0 |
| 18 | 4-trifluoromethoxyphenyl | 0 |

-continued

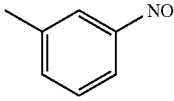

| Compound Number | R | n |
|---|---|---|
| 19 | 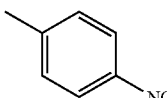 (3-nitrophenyl methyl) | 0 |
| 20 | 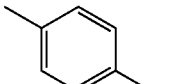 (4-nitrophenyl methyl) | 0 |
| 21 | 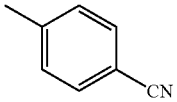 (4-COOMe phenyl methyl) | 0 |
| 22 | 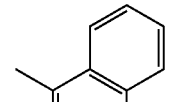 (4-CN phenyl methyl) | 0 |
| 23 | 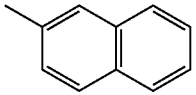 (1-naphthylmethyl) | 0 |
| 24 | 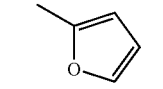 (2-naphthylmethyl) | 0 |
| 25 | 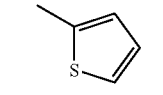 (2-furylmethyl) | 0 |
| 26 | 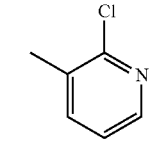 (2-thienylmethyl) | 0 |
| 27 | 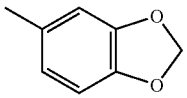 (2-chloro-3-pyridylmethyl) | 0 |
| 28 |  (benzodioxolylmethyl) | 0 |
| 29 | Me-C(Me)(Me)- (tert-butyl) | 0 |

-continued

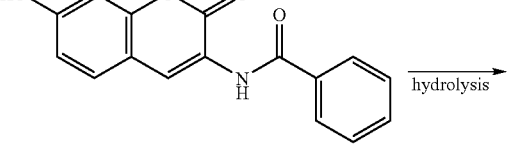

| Compound Number | R | n |
|---|---|---|
| 30 | 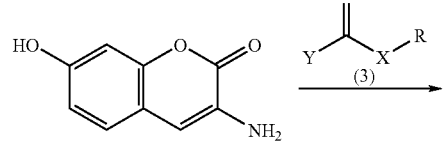 (phenyl) | 1 |

The compounds represented by the general formula (I) can be prepared, for example, by a method described in the reaction scheme 1.

<Reaction Scheme 1>

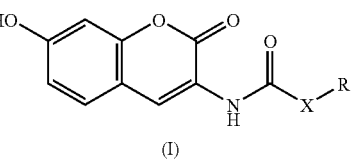

As for (7-hydroxy-2-oxo-2H-1-benzopyran-3-yl)benzamide (1) (Compound 1 shown on the above Table 1), method for preparation of the compound are already disclosed in, for example, "The Journal of Heterocyclic Chemistry", Volume 26, pp.1273-1275 (published in 1989).

By hydrolysis of the benzoyl group of N-(7-hydroxy-2-oxo-2H-1-benzopyran-3-yl)benzamide (1), 3-amino-7-hydroxy-2H-1-benzopyran-2-one (2) can be obtained. This reaction is carried out in the presence of an acid, with or without a solvent, at a reaction temperature of from room temperature to a refluxing temperature of a solvent used.

Examples of the acids include mineral acids such as hydrochloric acid and sulfuric acid, and Lewis acids such as triethyloxonium tetrafluoroborate. Any solvent can be used as long as it does not inhibit the reaction, and examples include tetrahydrofuran, 1,2-dimethoxyethane, 1,4-dioxane, methanol, ethanol, 1-propanol, 2-propanol, water, and acetic acid. These solvents can be used alone or as a mixed solvent.

The resulting 3-amino-7-hydroxy-2H-1-benzopyran-2-one (2) is then acylated to prepare the compounds represented by the general formula (I). This reaction is carried out by using the compound represented by the formula (3) (wherein Y represents a halogen atom, hydroxy group, a $C_1$ to $C_6$ alkoxy group which may be substituted, a $C_6$ to $C_{10}$ aryloxy group which may be substituted, a $C_1$ to $C_6$ alkoxycarbonyloxy group which may be substituted, a $C_6$ to $C_{10}$ aryloxycarbonyloxy group which may be substituted, aminooxy group which may be substituted, or hydroxyamino group which may be substituted at the nitrogen atom and/or the oxygen atom, A and X have the same meanings as those defined in the general formula (I)), in the presence or absence of an adjuvant for acylation, in the presence or absence of a base or an acid, with or without a solvent, at the reaction temperature of from −80° C. to a refluxing temperature of a solvent used.

Most of the compounds represented by the formula (3) are commercially available in the market, and the commercial products can be obtained and used without any treatment. Furthermore, general synthetic methods are disclosed in wide variety of books on experimental chemistry, for example, "Jikken Kagaku Koza (3rd Ed.)", "Zoku Jikken Kagaku Koza", "Shin Jikken Kagaku Koza", and "Jikken Kagaku Koza (4th Ed.)" (all edited by The Chemical Society of Japan, Maruzen). On the basis of these information, in can be understood that the aforementioned compounds can be readily prepared by those skilled in the art and used for preparation of the compounds of the present invention. As for the acylation, per se, general synthetic methods including the selection of the adjuvant for acylation, a base, an acid, and a solvent, and methods of use thereof are disclosed widely in the aforementioned books. Accordingly, those skilled in the art can readily conduct the acylation based on the information.

The compounds represented by the general formula (II) can be prepared according to the aforementioned preparation methods. In the examples of the specification, methods for preparation of typical compounds falling within the general formulas (I) or (II) are explained in detail. Accordingly, those skilled in the art can prepare any compound encompassed within the general formulas (I) or (II) by referring to the general explanations of the aforementioned preparation methods and specific explanations of the preparation methods of the examples, and by choosing appropriate starting materials, reagents, and reaction conditions and by adding appropriate modification and alteration to these methods, if necessary.

Medicaments of the present invention can be used to enhance the effect of cancer therapy based on the mode of action of DNA injury, including cancer chemotherapies by using anticancer agents and radiation therapies of cancer that induce DNA injury. Typical examples of anticancer agents that induces DNA injury include bleomycin, adriamycin, cisplatin, cyclophosphamide, and mitomycin C. Besides these derivatives, any of anticancer agents involving the mode of action of DNA injury can be targets of the medicaments of the present invention. The medicaments of the present invention may be used where either of a cancer chemotherapy using anticancer agents or a radiation therapy of cancer that induce DNA injury is solely carried out, or in a cancer therapy where a combination of these therapies is carried out.

Although it is not intended to be bound by any specific theory, the medicament of the present invention can bind to a protein kinase or its analogous enzyme that is activated after DNA injury, and terminate the functions of the enzyme to kill cancer cells. As a result, the medicaments can enhance the effect of the cancer therapy and can lower a dose of the anticancer agent and/or radiation for the cancer therapy, thereby reduce side effects resulting from the cancer therapy.

As the active ingredient of the medicament of the present invention, a hydrate or a solvate of the compounds represented by the aforementioned general formulas (I) or (II) or physiologically acceptable salts thereof may be used. Furthermore, when the compound contains one or more asymmetric carbon atoms, any of a pure form of optically active compound or any mixture of optically active compounds, or a racemate may be used. As the active ingredient of the medicament of the present invention, one or more kinds of substances selected from the group consisting of the aforementioned compound and a physiologically acceptable salt thereof, and a hydrate thereof and a solvate thereof may be used.

As the medicament of the present invention, the aforementioned substance, per se, may be administered. Preferably, the medicament may be administered as a pharmaceutical composition for oral or parenteral administration that may be prepared by methods well known to those skilled in the art. Examples of pharmaceutical compositions suitable for oral administration include tablets, capsules, powders, subtilized granules, granules, solution, and syrup, and examples of pharmaceutical compositions suitable for parenteral administration include injections, suppositories, inhalants, instillations, nasal drops, ointments, percutaneous absorbents, transmucosal absorptions, cream, and plaster.

The aforementioned pharmaceutical compositions can be prepared by adding physiologically and pharmaceutically acceptable additives. Examples of physiologically and pharmaceutically acceptable additives include excipients, disintegrators or disintegration aids, binders, lubricants, coating agents, colorants, diluents, base materials, dissolving aids or dissolution adjuvants, isotonizing agents, pH modifiers, stabilizers, propellants, and adhesives. One or more kinds of anticancer agents based on the mode of action of DNA injury may be added to the aforementioned pharmaceutical compositions.

A dose of the medicament of the present invention is not particularly limited. The dose may be selected appropriately depending on a kind of the active ingredient and a kind of a cancer therapy. Further, the dose may be appropriately increased or decreased depending on various factors that should be generally considered such as the weight and age of a patient, a kind and symptom of a disorder, and an administration route. Generally, for an oral administration, the medicament may be used in a range of 0.01 to 5,000 mg per day for an adult based on the weight of the active ingredient. The dose may be appropriately increased or decreased depending on age, conditions, symptoms of a patient. The aforementioned daily dose may be administered once a day or two to three times a day with suitable intervals, or alternatively, intermittently administered with intervals of several days. When the medicament is used as an injection, a dose may be about 0.001 to 100 mg per day for an adult based on the weight of the active ingredient.

EXAMPLES

The present invention will be explained more specifically with reference to the following examples. However the scope of the present invention is not limited to the following examples. The compound number in the following examples correspond to those in the table shown above. Compound 1 is a known compound, and was synthesized by the synthetic method disclosed in "Journal of Heterocyclic Chemistry", Volume 26, pp.1273-1275 (published in 1989). Compound 10 and 12 are both known and commercially available from Bionet Research Ltd. (United Kingdom). As for these compounds, the commercial products described above was purchased and subjected to the measurement of the biological activity.

Example 1

Preparation of 2-chloro-N-(7-hydroxy-2-oxo-2H-1-benzopyran-3-yl)benzamide (Compound 2)

(1) Preparation of 3-amino-7-hydroxy-2H-1-benzopyran-2-one.

A mixture of N-(7-hydroxy-2-oxo-2H-1-benzopyran-3-yl)benzamide (230 mg, 0.82 mmol), 1-propanol (6 ml) and concentrated hydrochloric acid (2 ml) was refluxed for 3 hours. Then, hydrochloric acid (2 ml) was added and the mixture was refluxed for further 7 hours. After cooling, the reaction mixture was poured into saturated aqueous sodium hydrogen carbonate and extracted with ethyl acetate. The ethyl acetate layer was washed successively with water and saturated brine, and after the layer was dried over anhydrous sodium sulfate, the residue obtained by evaporation of the solvent under reduced pressure was purified by column chromatography on silica gel (eluent: dichloromethane/ethyl acetate=2/1) to give the title compound as a yellow solid (127 mg, 87.7%).

$^1$H-NMR(DMSO-$d_6$, δ): 5.23(2H, s), 6.65-6.70(3H, m), 7.23(1H, d, J=8.4 Hz)

(2) Preparation of 2-chloro-N-(7-hydroxy-2-oxo-2H-1-benzopyran-3-yl)benzamide.

2-Chlorobenzoyl chloride (23.0 mg, 0.291 mmol) was added to a mixture of 3-amino-7-hydroxy-2H-1-benzopyran-2-one (50.0 mg, 0.282 mmol), and the mixture was stirred at room temparature for 1 hour. 1N hydrochloric acid (10 ml) was added, and the mixture was stirred. The precipitated crystal was filtered and washed successively with water and diisopropyl ether to give the title compound as a light brown crystal (48.8 mg, 54.8%).

$^1$H-NMR(CDCl$_3$+DMSO-$d_6$, δ): [2.59(a signal of DMSO)], 6.79(1H, d, J=2.1 Hz), 6.85(1H, dd, J=8.4, 2.4 Hz), 7.39-7.51(4H, m), 7.70(1H, dd, J=8.4, 1.8 Hz), [7.72(a signal of CHCl$_3$)], 8.73(1H, s), 9.19(1H, d, J=8.1 Hz), 10.05(1H, brs).

The compounds from Example 2 to Example 27 were prepared in the same manner as the method of Example 1(2). The yield and the physical properties data are described below.

Example 2

Preparation of 3-chloro-N-(7-hydroxy-2-oxo-2H-1-benzopyran-3-yl)benzamide (Compound 3)

Yield: 38.8%

$^1$H-NMR(CDCl$_3$+DMSO-$d_6$, δ): [2.58(a signal of DMSO)], 6.78(1H, d, J=2.4 Hz), 6.84(1H, dd, J=8.7, 2.4 Hz), 7.41(1H, d, J=8.4 Hz), 7.50(1H, t, J=7.5 Hz), 7.57(1H, ddd, J=7.8, 1.8, 1.5 Hz), [7.85(a signal of CHCl$_3$)], 7.86(1H, dt, J=7.5, 1.5 Hz), 7.95-7.96(1H, m), 8.61(1H, s), 9.23(1H, s), 10.12(1H, s).

Example 3

Preparation of 3-bromo-N-(7-hydroxy-2-oxo-2H-1-benzopyran-3-yl)benzamide (Compound 4)

Yield: 67.9%

$^1$H-NMR(CDCl$_3$+DMSO-$d_6$, δ): [2.59(a signal of DMSO)], 6.86-6.89(2H, m), [7.37(a signal of CHCl$_3$)], 7.39(1H, d, J=6.0 Hz), 7.42(1H, d, J=8.1 Hz), 7.71(1H, ddd, J=7.8, 1.8, 1.2 Hz), 7.83(1H, ddd, J=7.8, 1.8, 1.2 Hz), 8.06(1H, t, J=1.8 Hz), 8.73(1H, s), 8.76(1H, s), 9.79(1H, s).

Example 4

Preparation of 4-chloro-N-(7-hydroxy-2-oxo-2H-1-benzopyran-3-yl)benzamide (Compound 5)

Yield: 76.6%

$^1$H-NMR(CDCl$_3$+DMSO-$d_6$, δ): [2.58(a signal of DMSO)], 6.78(1H, d, J=2.4 Hz), 6.83(1H, dd, J=8.4, 2.1 Hz), 7.42(1H, d, J=8.4 Hz), 7.50(2H, d, J=8.1 Hz), 7.94(2H, d, J=8.4 Hz), 8.61(1H, s), 9.17(1H, d, J=5.4 Hz), 10.15(1H, d, J=7.8 Hz).

Example 5

Preparation of 4-fluoro-N-(7-hydroxy-2-oxo-2H-1-benzopyran-3-yl)benzamide (Compound 6)

Yield: 64.0%

$^1$H-NMR(CDCl$_3$+DMSO-$d_6$, δ): [2.59(a signal of DMSO)], 6.83(1H, d, J=2.4 Hz), 6.87(1H, dd, J=8.4, 2.4 Hz), 7.40(1H, d, J=8.4 Hz), [7.56(a signal of CHCl$_3$)], 7.79(2H, d, J=8.1 Hz), 8.08(2H, d, J=8.4 Hz), 8.73(1H, s), 9.00(1H, s), 9.99(1H, s).

Example 6

Preparation of 3,4-dichloro-N-(7-hydroxy-2-oxo-2H-1-benzopyran-3-yl)benzamide (Compound 7)

Yield: 73.8%

$^1$H-NMR(DMSO-$d_6$, δ): 6.78(1H, d, J=2.1 Hz), 6.84(1H, dd, J=8.1, 2.1 Hz), 7.60(1H, d, J=8.4 Hz), 7.82(1H, d, J=8.4 Hz), 7.92(1H, dd, J=8.1, 1.8 Hz), 8.19(1H, d, J=1.8 Hz), 8.42(1H, s), 9.98(1H, s), 10.52(1H, s).

Example 7

Preparation of N-(7-hydroxy-2-oxo-2H-1-benzopyran-3-yl)-2-methylbenzamide (Compound 8)

Yield: 51.5%

$^1$H-NMR(DMSO-$d_6$, δ): 2.42(3H, s), 6.77(1H, d, J=2.4 Hz), 6.83(1H, dd, J=8.7, 2.4 Hz), 7.27-7.35(2H, m), 7.38-7.43(1H, m), 7.48-7.53(1H, m), 7.60(1H, d, J=8.7 Hz), 8.49 (1H, s), 9.57(1H, s), 10.46(1H, s).

Example 8

Preparation of N-(7-hydroxy-2-oxo-2H-1-benzopyran-3-yl)-2-methylbenzamide (Compound 9)

Yield: 91.2%

$^1$H-NMR(DMSO-$d_6$, δ): 2.40(3H, s), 6.78(1H, d, J=2.1 Hz), 6.82-6.85(1H, m), 7.44(1H, s), 7.59(1H, d, J=8.7 Hz), 7.73-7.77(2H, m), 8.45(1H, s), 9.52(1H, s), 10.47(1H, d, J=0.9 Hz).

Example 9

Preparation of 4-(1,1-dimethylethyl)-N-(7-hydroxy-2-oxo-2H-1-benzopyran-3-yl)benzamide (Compound 11)

Yield: 53.6%

$^1$H-NMR(CDCl$_3$+DMSO-d$_6$, δ): 1.36(9H, s), [2.59(a signal of DMSO)], 6.85(1H, s), 6.87 (1H, dd, J=6.9, 2.1 Hz), [7.33(a signal of CHCl$_3$)], 7.36(1H, d, J=9.6 Hz), 7.53(2H, d, J=8.7 Hz), 7.85(2H, d, J=8.7 Hz), 8.70(1H, s), 8.80(1H, s), 9.68(1H, s).

Example 10

Preparation of N-(7-hydroxy-2-oxo-2H-1-benzopyran-3-yl)-4-(trifluoromethyl)benzamide (Compound 13)

Yield: 47.3%

$^1$H-NMR(CDCl$_3$+DMSO-d$_6$, δ): [2.57(a signal of DMSO)], 6.77(1H, d, J=2.4 Hz), 6.83(1H, dd, J=8.4, 2.4 Hz), 7.24(2H, t, J=8.4 Hz), 7.43(1H, d, J=8.7 Hz), [7.97(a signal of CHCl$_3$)], 7.99-8.04(2H, m), 8.59(1H, s), 9.20(1H, s), 10.17 (1H, brs).

Example 11

Preparation of N-(7-hydroxy-2-oxo-2H-1-benzopyran-3-yl)-[1,1'-biphenyl]-4-carboxamide (Compound 14)

Yield: 45.7%

$^1$H-NMR(CDCl$_3$+DMSO-d$_6$, δ): [2.53(a signal of DMSO)], 6.77(1H, d, J=2.1 Hz), 6.83(1H, dd, J=8.4, 2.1 Hz), 7.38-7.43(1H, m), 7.47-7.53(3H, m), 7.70-7.73(2H, m), 7.78-7.81(2H, m), 8.06(2H, d, J=8.4 Hz), [8.17(a signal of CHCl$_3$)], 8.57(1H, s), 9.41(1H, s), 10.30(1H, s).

Example 12

Preparation of N-(7-hydroxy-2-oxo-2H-1-benzopyran-3-yl)-2-methoxybenzamide (Compound 15)

Yield: 45.5%

$^1$H-NMR(DMSO-d$_6$, δ): 6.79(1H, d, J=2.1 Hz), 6.83(1H, dd, J=8.4, 2.1 Hz), 7.18(1H, t, J=7.8 Hz), 7.31(1H, d, J=8.7 Hz), 7.58-7.66(2H, m), 8.09(1H, dd, J=7.8, 1.8 Hz), 8.76(1H, s), 10.41(1H, s), 10.06(1H, s).

Example 13

Preparation of N-(7-hydroxy-2-oxo-2H-1-benzopyran-3-yl)-3-methoxybenzamide (Compound 16)

Yield: 53.5%

$^1$H-NMR(CDCl$_3$+DMSO-d$_6$, δ): [2.59(a signal of DMSO)], 3.89(3H, s), 6.81(1H, d, J=2.7 Hz), 6.86(1H, dd, J=8.4, 2.1 Hz), 7.12(1H, dt, J=7.2, 2.4 Hz), 7.39(1H, d, J=8.4 Hz), 7.43-7.48(3H, m), [7.66(a signal of CHCl$_3$)], 8.71(1H, s), 8.85(1H, s), 9.98(1H, brs).

Example 14

Preparation of N-(7-hydroxy-2-oxo-2H-1-benzopyran-3-yl)-3,4-dimethoxybenzamide (Compound 17)

Yield: 54.7%

$^1$H-NMR(CDCl$_3$+DMSO-d$_6$, δ): [2.59(a signal of DMSO)], 3.95(3H, s), 3.96(3H, s), 6.80(1H, d, J=2.1 Hz), 6.85(1H, dd, J=8.4, 2.1 Hz), 7.38(1H, d, J=8.44 Hz), 7.51-7.54(2H, m), [7.71(a signal of CHCl$_3$)], 8.68(1H, s), 8.83(1H, s), 9.99(1H, brs).

Example 15

Preparation of N-(7-hydroxy-2-oxo-2H-1-benzopyran-3-yl)-4-(trifluoromethoxy)benzamide (Compound 18)

Yield: 55.4%

$^1$H-NMR(DMSO-d$_6$, δ): 6.78(1H, d, J=2.4 Hz), 6.84(1H, dd, J=8.4, 2.4 Hz), 7.54(2H, d, J=8.1 Hz), 7.60(1H, d, J=8.7 Hz), 8.08(2H, d, J=8.7 Hz), 8.45(1H, s), 9.82(1H, s), 10.51 (1H, s).

Example 16

Preparation of N-(7-hydroxy-2-oxo-2H-1-benzopyran-3-yl)-3-nitrobenzamide (Compound 19)

Yield: 76.0%

$^1$H-NMR(CDCl$_3$+DMSO-d$_6$, δ): [2.59(a signal of DMSO)], 6.85-6.90(2H, m), 7.40(1H, d, J=8.7 Hz), [7.41(a signal of CHCl$_3$)], 7.75(1H, t, J=8.1 Hz), 8.28(1H, ddd, J=7.8, 1.8, 1.2 Hz), 8.43(1H, ddd, J=8.1, 2.4, 1.2 Hz), 8.75(1H, s), 8.81(1H, t, J=2.1 Hz), 9.08(1H, s), 9.90(1H, s).

Example 17

Preparation of N-(7-hydroxy-2-oxo-2H-1-benzopyran-3-yl)-4-nitrobenzamide (Compound 20)

Yield: 73.8%

$^1$H-NMR(DMSO-d$_6$, δ): 6.79(1H, s), 6.84(1H, d, J=8.4 Hz), 7.61(1H, d, J=8.4 Hz), 8.17(2H, d, J=8.4 Hz), 8.32-8.39 (2H, m), 8.47(1H, s), 10.09(1H, s), 10.54(1H, s).

Example 18

Preparation of 4-[[N-(7-hydroxy-2-oxo-2H-1-benzopyran-3-yl)amino]carbonyl]benzoic acid methyl ester (Compound 21)

Yield: 65.8%

$^1$H-NMR(CDCl$_3$+DMSO-d$_6$, δ): [2.59(a signal of DMSO)], 3.96(3H, s), 6.81(1H, d, J=1.8 Hz), 6.85(1H, dd, J=8.4, 2.1 Hz), 7.41(1H, D, J=8.7 Hz), [7.72(a signal of CHCl$_3$)], 8.02(2H, d, J=8.1 Hz), 8.15(2H, d, J=8.1 Hz), 8.70 (1H, s), 9.10(1H, s), 10.04(1H, brs).

Example 19

Preparation of 4-cyano-N-(7-hydroxy-2-oxo-2H-1-benzopyran-3-yl)benzamide (Compound 22)

Yield: 62.3%
$^1$H-NMR(DMSO-$d_6$, δ): 6.79(1H, d, J=1.8 Hz), 6.84(1H, dd, J=8.4, 1.8 Hz), 7.60(1H, d, J=8.4 Hz), 8.01-8.13(4H, m), 8.45(1H, s), 10.00(1H, s), 10.55(1H, s).

Example 20

Preparation of N-(7-hydroxy-2-oxo-2H-1-benzopyran-3-yl)-1-naphthalenecarboxamide (Compound 23)

Yield: 45.2%
$^1$H-NMR(DMSO-$d_6$, δ): 6.79(1H, d, J=2.1 Hz), 6.85(1H, dd, J=8.4, 2.1 Hz), 7.57-7.65(4H, m), 7.78(1H, dd, J=7.2, 0.9 Hz), 8.01-8.04(1H, m), 8.09(1H, d, J=8.1 Hz), 8.27-8.30(1H, m), 8.59(1H, s), 9.91(1H, s), 10.49(1H, s).

Example 21

Preparation of N-(7-hydroxy-2-oxo-2H-1-benzopyran-3-yl)-2-naphthalenecarboxamide (Compound 24)

Yield: 86.9%
$^1$H-NMR(CDCl$_3$+DMSO-$d_6$, δ): [2.59(a signal of DMSO)], 6.86-6.90(2H, m), [7.36(a signal of CHCl$_3$)], 7.40 (1H, d, J=9.0 Hz), 7.56-7.60(2H, m), 7.90-8.02(4H, m), 8.44 (1H, s), 8.85(1H, s), 8.90(1H, s), 9.78(1H, s).

Example 22

Preparation of N-(7-hydroxy-2-oxo-2H-1-benzopyran-3-yl)-2-furancarboxamide (Compound 25)

Yield: 90.2%
$^1$H-NMR(CDCl$_3$+DMSO-$d_6$, δ): [2.59(a signal of DMSO)], 6.60(1H, dd, J=3.6, 1.8 Hz), 6.83-6.88(2H, m), 7.25(1H, dd, J=2.7, 0.9 Hz), 7.36(1H, d, J=8.1 Hz), [7.44(a signal of CHCl$_3$)], 7.59(1H, dd, J=2.1, 0.9), 8.70(1H, s), 8.83(1H, t, J=2.1 Hz), 9.85(1H, s).

Example 23

Preparation of N-(7-hydroxy-2-oxo-2H-1-benzopyran-3-yl)-2-thiophenecarboxamide (Compound 26)

Yield: 61.7%
$^1$H-NMR(CDCl$_3$+DMSO-$d_6$, δ): [2.59(a signal of DMSO)], 6.85-6.88(2H, m), 7.16(1H, dd, J=4.8, 3.9 Hz), 7.35(1H, d, J=9.0 Hz), [7.39(a signal of CHCl$_3$)], 7.61(1H, dd, J=5.1, 1.2 Hz), 7.71(1H, dd, J=3.9, 1.2 Hz), 8.60(1H, s), 8.69(1H, s), 9.81(1H, s).

Example 24

Preparation of 2-chloro-N-(7-hydroxy-2-oxo-2H-1-benzopyran-3-yl)-3-pyridinecarboxamide (Compound 27)

Yield: 50.3%
$^1$H-NMR(CDCl$_3$+DMSO-$d_6$, δ): [2.59(a signal of DMSO)], 6.85-6.89(2H, m), [7.38(a signal of CHCl$_3$)], 7.39 (1H, d, J=8.1 Hz), 7.43(1H, dd, J=7.8, 4.5 Hz), 8.14(1H, dd, J=7.5, 2.1 Hz), 8.53(1H, dd, J=5.1, 2.1 Hz), 8.78(1H, s), 9.25(1H, s), 9.84(1H, s).

Example 25

Preparation of N-(7-hydroxy-2-oxo-2H-1-benzopyran-3-yl)-1,3-benzodioxole-5-carboxamide (Compound 28)

Yield: 40.0%
$^1$H-NMR(DMSO-$d_6$, δ): 6.15(2H, s), 6.78(1H, d, J=2.7 Hz), 6.83(1H, dd, J=8.4, 2.4 Hz), 7.06(1H, d, J=8.4 Hz), 7.49(1H, d, J=1.8 Hz), 7.57(2H, dt, J=8.4, 1.8 Hz), 8.40(1H, s), 9.45(1H, s), 10.51(1H, s).

Example 26

Preparation of N-(7-hydroxy-2-oxo-2H-1-benzopyran-3-yl)-2,2-dimethylpropanamide (Compound 29)

Yield: 69.2%
$^1$H-NMR(CDCl$_3$, δ): 1.34(9H, s), 6.04(1H, s), 6.82-6.86 (2H, m), 7.35(1H, d, J=8.1 Hz), 8.27(1H, s), 8.67(1H, s).

Example 27

Preparation of N-(7-hydroxy-2-oxo-2H-1-benzopyran-3-yl)benzeneacetamide (Compound 30)

Yield: 92.4%
$^1$H-NMR(CDCl$_3$+DMSO-$d_6$, δ): [2.59(a signal of DMSO)], 3.76(2H, s), 6.81-6.84(2H, m), 7.27-7.42(6H, m), [7.30(a signal of CHCl$_3$)], 8.08(1H, s), 8.62(1H, s), 9.52(1H, s).

TEST EXAMPLE

By using these compounds, effects on proliferation of Jurkat cells by sole administration and inhibitory effects on cell proliferation by administration in combination with bleomycin were examined. Materials and methods are as follows. Jurkat cells obtained from Dainippon Pharmaceutical Co. Ltd. were inoculated at about 10,000 cells per well in a 96 well culture plate, and incubated in 10% bovine fetal serum (Irvine Scientific) supplemented with RPMI1640(ICN) medium in 5% $CO_2$ incubator at 37° C. For the culture, each compound was added alone, or the culture was further added with bleomycin (Wako) to give a concentration of 5 μg/ml or 10 μg/ml. 36 hours after the incubation, the number of living cells was counted by the MTS method.

More specifically, 20 μl of CellTiter96™ AQueous One Solution (Promega) was added per one well, and after the cells were incubated for additional one hour, an absorbance at 490 nm was measured by using a microplate reader. The same culture added with DMSO as a solvent at final concentration of 0.25% was used as a control. The number of cells in the control was considered as 100% survival rate, and for each compound, survival rates by sole administration or a combined administration were calculated. Treatments solely with bleomycin at 5 μg/ml or 10 μg/ml gave about 5 to 10% of decrease in the survival rates of the Jurkat cells. Whilst, when the compound of the present invention coexisted, the survival rates of the Jurkat cells by bleomycin at 5 μg/ml or 10 μg/ml were remarkably decreased. The results are shown in the following table. In the table, ++ indicates observation of remarkable enhancement, + indicates moderated enhancement, and ± indicates weak enhancement.

| Compound | Activity |
|---|---|
| 1 | ± |
| 2 | + |
| 3 | + |
| 4 | + |
| 5 | ± |
| 6 | ± |
| 8 | + |
| 9 | + |
| 13 | + |
| 14 | ++ |
| 15 | ± |
| 16 | ± |
| 19 | ± |
| 20 | ± |
| 21 | ± |
| 22 | + |
| 23 | + |
| 24 | ± |
| 25 | ± |
| 26 | ± |
| 27 | ± |
| 28 | ± |
| 29 | ± |
| 30 | + |

INDUSTRIAL APPLICABILITY

In cancer treatments based on the mode of action of DNA injury, the medicaments of the present invention have inhibitory actions against protein kinases, which are activated in the cancer cells suffered from the DNA injury, to kill said cancer cells. The medicaments of the present invention thus enhance the effect of a cancer therapy based on the mode of action of DNA injury and reduce a dose of an anticancer agent and/or radiation. Therefore, the medicaments can reduce side effects resulting from the cancer therapy.

What is claimed is:

1. A compound represented by the general formula (II) or a salt thereof:

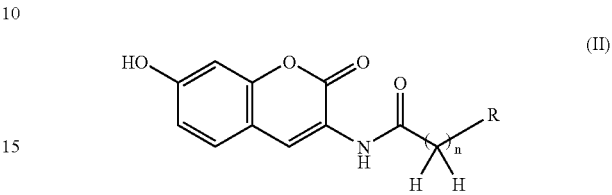

wherein n represents an integer of from 0 to 2; R represents a $C_6$ to $C_{10}$ aryl group which may be substituted or a 4 to 10-membered monocyclic or bicyclic and unsaturated, partly saturated, or completely saturated heterocyclic group which may be substituted, wherein said heterocyclic group comprises as ring-constituting atoms 1 to 4 hetero atoms selected from the group consisting of nitrogen atom, oxygen atom, and sulfur atom; provided that the compound wherein n is 0; and R is unsubstituted phenyl group, 4-methylphenyl group, 3-(trifluoromethyl)phenyl group, 4-methoxyphenyl group, or 2,4-dichlorophenyl group is excluded.

2. A medicament comprising as an active ingredient a compound represented by claim 1 or a physiologically acceptable salt thereof.

* * * * *

UNITED STATES PATENT AND TRADEMARK OFFICE
CERTIFICATE OF CORRECTION

PATENT NO. : 7,411,076 B2  Page 1 of 1
APPLICATION NO. : 10/488254
DATED : August 12, 2008
INVENTOR(S) : S. Muto et al.

It is certified that error appears in the above-identified patent and that said Letters Patent is hereby corrected as shown below:

On the Title page of the printed patent, at Item (30), Foreign Application Priority Data, the following data was omitted and should be included:

Japanese Application No. 2001-276940 filed September 12, 2001.

Signed and Sealed this

Twenty-fourth Day of March, 2009

JOHN DOLL
*Acting Director of the United States Patent and Trademark Office*